United States Patent
Hodgkinson

(10) Patent No.: US 6,353,106 B1
(45) Date of Patent: Mar. 5, 2002

(54) PROCESS FOR THE PRODUCTION OF TRIFLUOROMETHYLTROPANONE CYANOHYDRIN

(75) Inventor: Ian Hodgkinson, Holmforth (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/857,411

(22) PCT Filed: Nov. 10, 1999

(86) PCT No.: PCT/GB99/03754
§ 371 Date: Aug. 24, 2001
§ 102(e) Date: Aug. 24, 2001

(87) PCT Pub. No.: WO00/34275
PCT Pub. Date: Jun. 15, 2000

(30) Foreign Application Priority Data

Dec. 7, 1998 (GB) ............................................. 9913455

(51) Int. Cl.$^7$ ............................................ C07D 451/06
(52) U.S. Cl. ...................................................... 546/127
(58) Field of Search ........................................ 546/127

(56) References Cited

FOREIGN PATENT DOCUMENTS

WO WO 96/37494 11/1986

OTHER PUBLICATIONS

Nazarov, et al. (1956) "Heterocyclic Compounds. 45. Cyanhydrins of Gamma–Piperidones, Tetrahydro–Gamma–Pyrones and Tetrahydro–Gamma–Thiopyrones, Stereochemistry of the Cyanhydrin Synthesis" J. Gen Chem. 3545–3554.

Della, et al. (1990) "Rearrangement of Substituted Bicyclo '2.2.1!hex–2–yl Mesylates Under Solvolytic Conditions" Aust. J. Chem. 43:1231–1244.

Iorio, et al. (1984) "Nitrogen analogues of phencyclidine: 1–alkyl–4–phenyl–4–(1–piperidinyl)piperidines" Farmaco Ed. Sci 39:599–611.

Sasaki, et al. (1978) "Synthesis of adamantane derivatives—38. Synthesis of 1,3–bishomoadamantane via ring–expansion of homoadamantan–2–one and homoadamant–4–en–2–one" Tetrahedron 34:67–71.

Binmore, et al. (1994) "Homolytic Reactions of Homocubane and Basketane: Rearrangement of the 9–Basketyl Radical by Multiple beta–Scissions" J. Am. Chem. Soc. 116:2759–2766.

Burgos, et al. (1992) "Synthesis, Structural Conformational and Biochemical Study of some 3beta–Acyloxytropan–3alpha–carboxylic Acid Hydrochlorides" 29:1821–1827.

Del Campo, et al. (1984) 145. Synthese facile de derives du diphenyl–2,4–aza–3–bicyclo '3.3.1? nonane et du dipheny–7,9–aza–8–bicyclo '4.3.1?decane Helv. Chim. Acta 67:1291–1297.

Matsuda, et al. (1992) "A Practical Synthesis of threo–3–Amino–2–hydroxycarboxylic Acids" Bull. Chem. Soc. Jpn 65:360–365.

Julia, et al. (1979) "Asymmetric Induction by Phase–Transfer Catalysis using Chiral Catalysts. Synthesis of 1,2–dichloroalkanes and acetylcyanohydrins" Tetrahedron Lett. 2171–2174.

Mcintosh, J.M. (1977) "Phase–Transfer Catalyzed Formation of Cyanohydrin Ethers and Acetates" Can. J. Chem. 55:4200–4205.

*Primary Examiner*—Patricia L. Morris
(74) *Attorney, Agent, or Firm*—Hale and Dorr LLP

(57) ABSTRACT

A process for the preparation of a compound of formula (I), the process comprising the steps of (i) adding a solution of a compound of formula (II) in aqueous hydrochloric acid to an aqueous solution of sodium cyanide at a temperature in the range −5 to 10° C., and (ii) mixing the resulting mixture at a pH in the range 8.5–9.5 and a temperature in the range −5 to 5° C. for 15–24 hours under efficient agitation conditions, the concentration of sodium cyanide in the resulting mixture being greater than 2.4 molar.

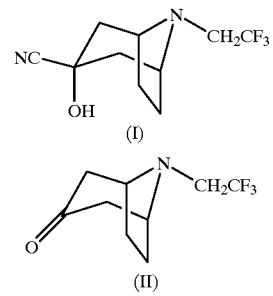

6 Claims, No Drawings

PROCESS FOR THE PRODUCTION OF TRIFLUOROMETHYLTROPANONE CYANOHYDRIN

This application is a 371 of PCT/GB99/03754 filed Nov. 10, 1999.

The present invention concerns a process for preparing 3-cyano-8-substituted-8-azabicyclo[3.2.1]octanes. 3-Cyano-8-substituted-8-azabicyclo[3.2.1]octanes are useful as intermediates for certain insecticides (see, for example, WO 96/37494).

The present invention provides a process for the preparation of a compound of formula (I):

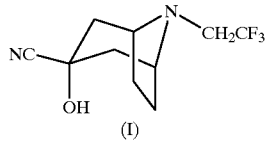

the process comprising the steps:
i. adding a solution of a compound of formula (II):

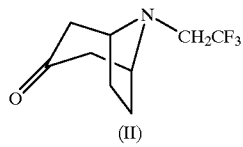

in aqueous hydrochloric acid to an aqueous solution of sodium cyanide at a temperature in the range −5 to 10° C.; and, ii. mixing the resulting mixture at a pH in the range 8.5–9.5 and a temperature in the range −5 to 5° C. for 15–24 hours under efficient agitation conditions, the concentration of sodium cyanide in the resulting mixture being greater than 2.4 molar.

The solution of the compound of formula (II) in step (i) is preferably prepared by dissolving the compound of formula (II) in concentrated (about 36%w/w) hydrochloric acid and then adding an appropriate amount of cold water (preferably below 5° C.).

During Step (ii) the initial reaction mixture of a precipitate of compound (II) and compound (I) and the endo-cyano epimer of compound (I) is slowly converted to compound (I). In order to promote this two-phase reaction efficient agitation conditions sufficient to break the particles forming the solid phase (preferably high-shear conditions to enable a greater degree of particle breakage) are required. Such agitation conditions are fully described in Chapter 6 of "Mixing—principles and application" by S. Nagata, John Wiley 1975.

In one aspect the present invention provides a process as hereinbefore described wherein the pH range in step (ii) is 9.0–9.3.

In another aspect the present invention provides a process as hereinbefore described wherein, in step (ii), the concentration of sodium cyanide in the resulting mixture is greater than 3.5 molar.

In a further aspect the present invention provides a process as hereinbefore described wherein the agitation conditions of step (ii) are sufficient to break the particles of a precipitate forming a solid phase. In a still further aspect the present invention provides a process as hereinbefore describedwherein the agitation conditions are high-shear conditions.

In another aspect the present invention provides a process as hereinbefore described wherein step (ii) is conducted at a temperature in the range 0–2° C.

In a further aspect the present invention provides a process for the preparation of a compound of formula (I) comprising the steps:
i. adding a solution of a compound of formula (II) in aqueous hydrochloric acid to an aqueous solution of sodium cyanide at a temperature in the range −5 to 10° C. (preferably about 0° C.); and, ii. mixing the resulting mixture at a pH in the range 8.5–9.5 (preferably 9.0–9.3) and a temperature in the range −5 to 5° C. (preferably about 0–2° C.) for 15–24 hours (preferably 17–20 hours) under efficient agitation conditions, the concentration of sodium cyanide in the resulting mixture being greater than 2.4 molar (preferably greater than 3.5 molar). In the following Examples, Examples 1 to 3 illustrate the invention.

EXAMPLE 1

This Example illustrates the preparation of 3-exo-cyano-3-endo-hydroxy-8-(2,2,2-trifluoroethyl)-8-azabicyclo [3.2.1]octane (that is, equatorial cyano).

A 250 ml split neck jacketed reactor was equipped with overhead stirrer, thermometer, and vented to a hypochlorite scrubber. To the reactor was charged water (50 ml), followed by sodium cyanide (13.42 g, 265 mmol) and the solution was cooled to 0° C. 8-(2,2,2-Trifluoroethyl)-8-azabicyclo[3.2.1] octan-3-one (5.0 g, 24 mmol) and concentrated hydrochloric acid (22.1 g, 221 mmol) were mixed and the resultant brown hydrochloride solution was charged to the reactor over 1.25 hour (via syringe pump). A cream coloured precipitate formed during the addition. The reaction mixture was agitated overnight, then the pH was adjusted from pH 8.7 to pH 4.8 using hydrochloric acid. Diethyl ether (40 ml) was added (the pH fell to 2 and was re-adjusted to 5.6 with 70% sodium hydroxide). The organic phase was separated off and the aqueous extracted with a further portion of diethyl ether (40 ml). The combined organic extracts were washed with pH 5.5 water (modified with hydrochloric acid), stabilised (2 drops sulphuric acid), dried (MgSO$_4$), filtered, re-stabilised and concentrated under reduced pressure to give a brown water-wet semi-solid. The material was re-dissolved in diethyl ether, dried (MgSO$_4$), filtered, stabilised and concentrated under reduced pressure to give the title compound as a pale brown solid (3.0 g, 85% strength, 45% yield).

EXAMPLE 2

This Example illustrates the preparation of 3-exo-cyano-3-endo-hydroxy-8-(2,2,2-trifluoroethyl)-8-azabicyclo[3.2.1 ]octane (I, equatorial cyano).

Water (312 g) was charged to a 750 ml jacketed reactor (approximately 7 cm in diameter) fitted with a 5 cm diameter agitator. Sodium cyanide (107.4 g) was added and the mixture was stirred until the sodium cyanide dissolved. The temperature of the solution was reduced to 0° C. using jacket cooling and the agitation speed was set at 500 rpm.

8-(2,2,2-Trifluoroethyl)-8-azabicyclo[3.2.1]octan-3-one (II, 40.8 g) was dissolved in hydrochloric acid (36%w/w, 177 g), the solution was diluted with ice cold water (80 g) and then charged to the sodium cyanide solution over 30 minutes, keeping the temperature below 5° C. with jacket cooling. After confirming that the pH of the mixture was in the range 9.0–9.3, stirring was continued for 18hours at 0–2° C.

Analysis by NMR showed the conversion of (II) to be 98% and the process selectivity for 3-exo-cyano-3-endo-hydroxy-8-(2,2,2-trifluoroethyl)-8-azabicyclo[3.2.1]-octane to be 95%.

In this Example the final concentration of unreacted sodium cyanide relative to the amount of water present was calculated to be 3.78 molar.

EXAMPLE 3

This Example illustrates the preparation of 3-exo-cyano-3-endo-hydroxy-8-(2,2,2-trifluoroethyl)-8-azabicyclo[3.2.1]octane (I, equatorial cyano).

A similar experiment to Example 2 was carried out using additional water such that the final sodium cyanide concentration was only 2.46 molar. In this case the conversion of (II) after 18 hours was 93%.

EXAMPLE 4

This Example illustrates the preparation of 3-exo-cyano-3-endo-hydroxy-8-(2,2,2-trifluoroethyl)-8-azabicyclo[3.2.1]octane (I, equatorial cyano).

A similar experiment to Example 2 was carried out using additional water such that the final sodium cyanide concentration was only 1.63 molar. In this case the conversion of (II) after 18 hours was only 42%.

Chemical Formulae used in the Description

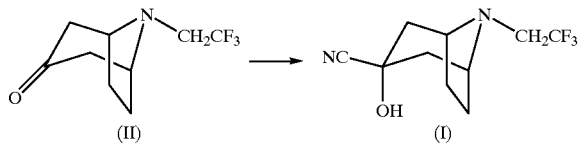

What is claimed is:

1. A process for the preparation of a compound of formula (I):

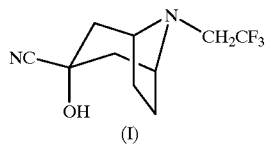

the process comprising the steps:

i. adding a solution of a compound of formula (II):

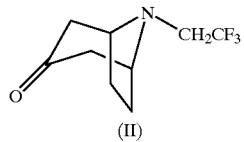

in aqueous hydrochloric acid to an aqueous solution of sodium cyanide at a temperature in the range −5 to 10° C.; and, ii. mixing the resulting mixture at a pH in the range 8.5–9.5 and a temperature in the range −5 to 5° C. for 15–24 hours under efficient agitation conditions, the concentration of sodium cyanide in the resulting mixture being greater than 2.4 molar.

2. A process as claimed in claim 1 wherein the pH range in step (ii) is 9.0–9.3.

3. A process as claimed in claim 1, wherein, in step (ii), the concentration of sodium cyanide in the resulting mixture is greater than 3.5 molar.

4. A process as claimed in claim 1, wherein the agitation conditions of step (ii) are sufficient to break the particles of a precipitate forming a solid phase.

5. A process as claimed in claim 1, wherein the agitation conditions are high-shear conditions.

6. A process as claimed in claim 1, wherein step (ii) is conducted at a temperature in the range 0–2° C.

* * * * *